(12) United States Patent
Pfeiffer et al.

(10) Patent No.: US 6,223,069 B1
(45) Date of Patent: Apr. 24, 2001

(54) PROCESS AND DEVICE FOR NON-INVASIVELY DETERMINING CEREBRAL BLOOD FLOW BY NEAR-INFRARED SPECTROSCOPY

(75) Inventors: Ulrich J. Pfeiffer; Wolfgang Kubler; Alwin E. Goetz, all of Munich (DE)

(73) Assignee: Pulsion Medical Systems AG (DE)

( * ) Notice: Subject to any disclaimer, the term of this patent is extended or adjusted under 35 U.S.C. 154(b) by 0 days.

(21) Appl. No.: 09/254,153

(22) PCT Filed: Aug. 29, 1997

(86) PCT No.: PCT/EP97/04725
§ 371 Date: Jul. 2, 1999
§ 102(e) Date: Jul. 2, 1999

(87) PCT Pub. No.: WO98/08434
PCT Pub. Date: Mar. 5, 1998

(30) Foreign Application Priority Data

Aug. 29, 1996 (DE) .............................. 196 35 038

(51) Int. Cl.[7] .................................................. A61B 5/026
(52) U.S. Cl. ........................ 600/431; 600/504; 600/310
(58) Field of Search .................................. 600/431, 504, 600/310, 314, 317; 356/300, 302, 51, 39

(56) References Cited

U.S. PATENT DOCUMENTS

| 4,805,623 | 2/1989 | Jobsis . |
| 5,494,031 | * 2/1996 | Hoeft ................................ 600/431 |
| 5,564,418 | * 10/1996 | Ozaki et al. ...................... 600/310 |
| 5,995,857 | * 11/1999 | Toomim et al. .................. 600/322 |

FOREIGN PATENT DOCUMENTS

| 41 30 931 | 3/1993 | (DE) . |
| 374844 | * 6/1990 | (EP) ................................... 600/310 |
| 502 270 A1 | 9/1992 | (EP) . |
| 615 723 A1 | 9/1994 | (EP) . |
| 96 16594 | 6/1996 | (WO) . |

OTHER PUBLICATIONS

Edwards, A.D. et al, "Measurement of Hemoglobin Flow and Blood Flow By Near–Infrared Spectroscopy", Journal of Applied Physiology, 75(4) 1884–9, Oct.1993.*

Roberts et al., *the Lancet*, vol. 342, 1993 at 1425.

\* cited by examiner

*Primary Examiner*—John A. Jeffrey
(74) *Attorney, Agent, or Firm*—Nixon Peabody LLP; Donald R. Studebaker

(57) ABSTRACT

A process and device for noninvasive measurement of cerebral blood flow simultaneously determines of a blood flow index which is directly proportional to the blood flow. Cerebral surge kinetics of an intravenously injected indicator dye with absorption properties in the near-infrared spectrum is sensed by near-infrared spectroscopy and the arterial surge kinetics is sensed by pulse densitometry. A device for carrying out this process consists of a multichannel apparatus having at least two near-infrared spectroscopes, each having two pulsed monochromatic light sources, a measuring and a reference wavelength, in the range of the near-infrared spectrum; one or more light sensors connected to a photomultiplier; and a noninvasive measuring device which determines, by pulse densitometry, the concentration of the tracer in the arterial blood of the circulatory system.

17 Claims, 4 Drawing Sheets

PROCESS AND DEVICE FOR NON-INVASIVELY DETERMINING CEREBRAL BLOOD FLOW BY NEAR-INFRARED SPECTROSCOPY

BACKGROUND OF THE INVENTION

1. Field of the Invention

The present invention relates to a process and system for non-invasively measuring cerebral blood flow by near-infrared spectroscopy and more particularly to near-infrared spectroscopy which uses the intravenous administration of a tracer dye.

2. Description of the Related Art

Near-infrared spectroscopy (NIRS), was described for the first time in 1977 by Jöbsis (Jöbsis, F. F.: Science 198 (1977), 1264–1267), and represents a relatively new method that makes it possible to non-invasively detect changes in the concentration of chromophores having absorption properties in the near-infrared spectrum in the tissue. The light emitted by a laser at the surface of the body in the near-infrared spectrum ($\lambda$=700–1000 nm) can, in contrast to visible light, penetrate endogenous tissue up to a depth of 6 cm. See Van der Zee, P. et al.: Adv. Exp. Med. Biol. 316 (1992), 143–153. In doing so, part of the light is scattered and reflected and can again be detected at the surface of the body by a photomultiplier. Chromophores in the tissue with absorption properties in the range of the emitted light are able, depending on their concentration, to absorb the incident light and thus reduce the amount of light emitted. According to the Beer-Lambert law, the concentration of chromophores in the tissue can be deduced from the light absorption, i.e., the optical density of the tissue.

A noninvasive method for measuring cerebral blood flow by near-infrared spectroscopy (NIRS) was developed in 1988 by Edwards et al. (Edwards, A. D. et al.: The Lancet 2 (1988), 770–771).

The method developed by Edwards et al. uses $HbO_2$ as a tracer substance for measuring cerebral blood circulation. The concentration of the tracer in the blood is rapidly raised by a sudden increase in the oxygen content of inhaled air ($FiO_2$). The surge of the "tracer" in the cerebral circulation is detected by NIRS and, based on the Fick principle, is calculated by comparison with the surge of cerebral blood flow detected peripherally by pulsoximetry (Edwards, A. D. et al.: J. Appl. Physiol. 75 (1993), 1884–1889; Elwell, C. E. et al.: Adv. Exp. Med. Biol. 317 (1992), 235–245; Elwell, C. E. et al.: J. Appl. Physiol. 77 (1994), 2753–2760; Elwell, C. E. et al.: Acta Neurosurgery 59 (1993), 74–80). The methodology is validated by comparison with a plethysmographic blood flow measurement at the underarm (Edwards, A. D. et al.: J. Appl. Physiol. 75 (1993), 1884–1889).

One drawback of the method described by Edwards is that the surge of the tracer substance cannot be precisely controlled, since the rapid oxygenation of hemoglobin with the increase in $FiO_2$ depends on ventilation. Further, the concentration of the tracer substance, even with the most rapid increase in $HbO_2$, will not increase rapidly enough to achieve optimal determination of the CBF (cerebral blood flow). To achieve a measurable increase in $HbO_2$ by increasing $FiO_2$, first a lowering of the $HbO_2$ by hypoventilation is necessary. However, this generally does not occur in traumatized patients whom a measurement of the CBF would be clinically relevant.

Another drawback of the method described by Edwards et al. is that it is an invasive method. Because it requires the implantation of an additional intravascular, fiber-optic measuring catheter it is not suited for rapid, noninvasive measurement of cerebral blood flow.

For these reasons, Roberts et al. (Roberts, I. et al.: The Lancet 342 (1993), 1425) modified the methodology by using, instead of $HbO_2$, an intravenously administered dye as the tracer substance. The dye indocyanine green (1-[sulfobutyl]-3,3-dimethyl-2-[7-[-4-sulfobutyl]-3,3-dimethyl-4,5-benzoindolinylidene-[2]]-heptatriene-[1,3,5]-yl]4,5,benzoindolium) with a molecular weight of 774,97 Daltons (Cherrick, G. R. et al.: J. Clin. Invest. 39 (1960), 592–600), has a maximum absorption rate of about 805 nm and thus lies in the spectrum of near-infrared light (Landsman, M. L. J. et al.: J. Appl. Physiol. 40 (1976), 575–583). After intravenous administration, the dispersion of indocyanine green by the 95% bonding to plasma proteins (Muckle, T. J.: Biochem. Med. 15 (1976), 17–21), especially α-lipoproteins, is strictly limited to the intravascular compartment (Cherrick, G. R. et al.: J. Clin. Invest. 39 (1960), 592–600). In this way, it is extraordinarily suited as an intravascular tracer. Since it is eliminated quickly by the liver from the circulatory system (Cherrick, G. R. et al.: J. Clin. Invest. 39 (1960), 592–600), repeated measurements at brief intervals are possible. The particular light-absorbing properties of indocyanine green in the near-infrared spectrum make it possible to detect its presence by near-infrared spectroscopy.

Roberts et al. tried to use, instead of the endogenous tracer $HbO_2$, an intravenous bolus injection of indocyanine green as the tracer substance and again, using the Fick principle, to calculate cerebral blood flow. For this purpose, the surge of indocyanine green in the cerebral vascular system was detected by NIRS and simultaneously the surge of the dye in the arteries was recorded by an invasively implanted arterial catheter. The cerebral blood flow was then determined as $CBF=k(Q(t)/(\int_0^t(Pa)dt))$, where CBF is the cerebral blood flow [ml/(100 g×min)], k is the constant consisting of the molecular weight of indocyanine green and the density of the cerebral tissue, Q is the accumulation of tracer in the brain measured by NIRS, and P(a) is the arterial concentration of the tracer measured invasively by an intravascular, fiber optic catheter.

In contrast, the device according to the present invention uses two spectroscopes and thus makes it possible to simultaneously measure the relative circulation of blood in the brain through both hemispheres. The near-infrared spectroscope NIRO 500 produced by Hamamatsu Photonics used by Roberts et al. comprises four pulsed lasers in the near-infrared spectrum range, whereas in the present device only two pulsed monochromatic light sources are used for each hemisphere of the brain, one for a measuring wavelength and one for a reference wavelength in the near-infrared spectrum range.

Finally, the arterial dye curve is measured in the device described by Roberts et al. by a fiber optic catheter implanted invasively intra-arterially. The system of the present invention in contrast uses noninvasive measurement of the arterial dye curve by a measuring device using pulse densitometry. The invasiveness of the device and process described by Roberts et al. represents an essential difference compared to the system and process of the present invention, since the implantation of a fiber optic catheter is a surgical procedure having the medical risks of infection, perforation or thrombosis/embolism. In contrast, pulse densitometry is performed non-invasively and thus does not encompass any of the prior art risks described above.

With respect to the measuring procedure, the method used by Roberts et al. clearly differs from the one described herein. In the first place the cerebral blood flow is calculated on the basis of the Fick principle, whereas the process of the present invention is performed by doing a transport function analysis of the indicator dilution curve by deconvolution and subsequently determining a relative blood flow index based on the transcerebral dye transport function. Both processes for measuring cerebral blood flow by near-infrared spectroscopy and intravenous administration of a tracer dye were not validated, i.e., the measurement values obtained were not compared with an independent method. In a briefly conducted study, (Kuebler, W. M. et al.: Int. J. Microcirc.: Clin. Exp. 16 Sl (1996), 223) it was proven for the first time that the measurement values obtained with one of the two methods described above in no way reflects cerebral blood circulation, but rather are the expression of cardiac volume, of which brain blood circulation is independent because of its ability to regulate itself over a wide range.

Proctor et al. (Proctor, H. J. et al.: Surgery 96 (1984), 273–279) used, for the first time in 1984, the intravenous administration of indocyanine green as a tracer substance for determining cerebral blood circulation by near-infrared spectroscopy. They calculated the integral using the surge curve measured by NIRS after intravenous administration of a defined bolus of indocyanine green.

A new process for measuring cerebral blood flow with the aid of a dual indicator dilution method (Mielck, F. et al.: Abstract Book, The European Association of Cardiothoracic Anesthesiologists 11 (1996), 7), makes it possible to quickly and repeatedly determine the CBF of a sickbed patient. Like Edwards, this method is based on an invasive measurement using an intravascular indwelling catheter and offers no breakdown by brain region.

The process disclosed by Hoeft, like Roberts et al., is also based on deconvolution (international AZ PCT/DE95/01690) or Mielck et al., but uses a dual indicator dilution process by determination of a dye kinetic and a thermodilution, and cerebral blood flow in particular is based solely on the thermodilution method (highly diffusible tracer). In contrast, the measurement described in the present invention is based solely on the determination of a dye kinetic (intravascular tracer). The device and measuring process of the Hoeft application differs completely from the present invention especially with regard to the invasiveness of the measurement means which includes surgical implantation of two combined fiber optic-thermistor catheters. Common to both measuring processes is the determination of a transcerebral transport function of the indicator used in each case by calculating a so-called convolution integral by a standardized deconvolution process. The transport functions calculated this way, which contain the characteristic transmission properties of a system, are widespread in natural and engineering sciences as so-called weight functions (Hoeft, A., Dilution Techniques and Fick Principle. In: Monitoring in Anaesthesia and Intensive Medicine, edited by W.F. List, H. Metzler, and T. Pasch, Berlin, Heidelberg, New York: Springer Verlag, 1995 p. 250–291).

Thus, until the present invention, no method has been developed that allows, on an in bed patient, rapid, repeated, noninvasive measurement, broken down by region, of cerebral blood flow (CBF), the adequate regulation of which is an unconditional prerequisite for intact neuronal activity of the brain.

SUMMARY OF THE INVENTION

It is an object of the present invention to make available a process and system, for measuring cerebral blood flow by near-infrared spectroscopy using intravenous administration of a tracer dye, which does not exhibit the drawbacks of the prior art methods.

Another object of the present invention is to allow for the noninvasive, rapid, user-friendly, economical and repeated measurement of cerebral blood flow in a patient in the sick bed, without impairing the care of the patient (e.g., by hypoventilation).

Still another object of the present invention is to measure CBF simultaneously for two or more regions of the brain, e.g., for both hemispheres of the brain.

In accomplishing these and other objectives of the invention, a surge of an intravenously injected bolus of a tracer substance having absorption properties in the near-infrared spectrum is detected simultaneously and noninvasively in several regions of the brain, in both brain hemispheres for example, by near-infrared spectroscopy. The arterial blood of the circulatory system is measured using pulse densitometry of arterial dye. The transcerebral transport function is calculated by the development of arterial and cerebral surge kinetics. Based on these kinetics a blood flow index is determined that is directly proportional to cerebral blood flow.

The system according to the present invention is characterized by a multichannel device having two or more near-infrared spectroscopes. Each spectroscope includes at least one photomultiplier and two pulsed, monochromatic light sources in the wavelength of the near-infrared spectrum. One of the light sources, measuring wavelength, corresponds as much as possible to the absorption maximum of the tracer substance used. The other light source, reference wavelength, has a wavelength at which the tracer substance has as few absorption properties as possible. A noninvasive measuring device determines by pulse densitometry the tracer concentration in the arterial blood of the circulatory system.

Other features and advantages of the present invention will become apparent from the following description of the invention which refers to the following drawings.

DETAILED DESCRIPTION OF THE PREFERRED EMBODIMENT

Figure 1A:
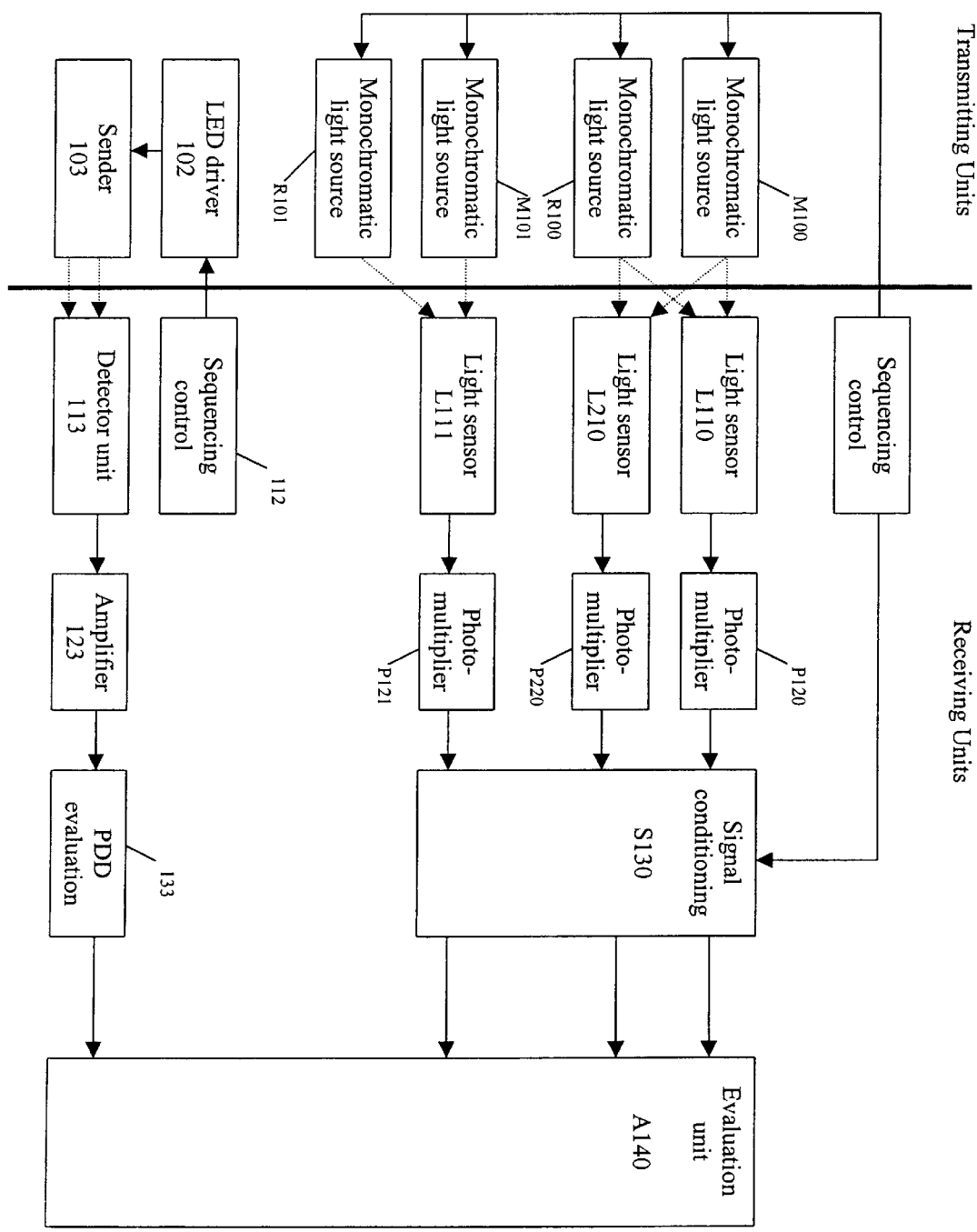
FIG. 1A is a block diagram of the process of the present invention.

The principle of blood circulation measurement on which the invention is based is the following: The passage of a tracer bolus through the cerebral circulatory system changes the optical density of the brain in the absorption range of the tracer substance used. This change in the optical density over time can be quantified by near-infrared spectroscopy and corresponds to the cerebral dye curve. The transcerebral transport function that describes the characteristic transmission properties of the system and is designated as weight function in the terminology of engineering sciences, can be determined by the "development" of the cerebral dye curve with the arterial dye curve in the circulatory system being measured by noninvasive pulse densitometry. The correlation between transport function g(t), arterial dye curve a(t) and cerebral dye curve c(t) is expressed by the following convolution integral:

$$c(t) = {}_0\int^\infty g(t-u)a(u)\,du,$$

where u is an auxiliary variable of the integration.

The determination of transcerebral transport function g(t) by the "development" of a(t) and c(t) can be performed by a process without modelling, but the use of modelling functions is numerically better. If the basic form of the transport function is known and able to be described by a function, then for measured curve pairs of a(t) and c(t), the parameters of the subordinate transport functions can be determined by an iterative, nonlinear matching process. For this purpose, according to the principle of the smallest squares and using iterative variation of the parameters of transport function g(t), the squares of the differences between measured cerebral concentrations and the result of development of the arterial curve with the transport function are minimized, which are determined by the following expression:

$$[c(t) - {}_0\int^\infty g(t-u)a(u)du]^2$$

Importantly, because of the different measuring processes of the cerebral and arterial dye curve, their dimensions are different and should not be allowed to mutually cross over into one another. Accordingly, dimension [ml/min] results for transcerebral transport function g(t).

Logarithmic normal distributions have proven successful in describing intravascular dye transport functions. For this reason, the following equation can be chosen for g(t):

$$g(t) = g_{lognor}(t, mtt, \sigma) = (1/\sqrt{2\pi}\sigma t)e^{-(ln(t/mtt)+\sigma^2/2)^2/2\sigma^2}$$

where mtt is the average transit time of the dye and σ is the relative dispersion of the dye.

Here, the average transit time of the dye and the transport function itself are relative not to the arteriovenous transit of the indicator, but only to its surge in the tissue in which the dye curve is determined by near-infrared spectroscopy.

If, as in the brain with gray and white substances, there exists intravascular compartments with blood flowing through them at varying rates, the transport function can be represented by the sum of two logarithmic normal distributions according to the following formula:

$$g(t) = \Sigma \alpha_i g_{log\,nori}(t, mtt_i, \sigma_i).$$

From the transcerebral transport function of tracer g(t) cerebral blood circulation can be deduced in the following way.

From the ratio of the maximum surge and the surge time of the dye in the transcerebral transport function after injection of the bolus of dye, a blood flow index is calculated that is directly proportional to the actual blood circulation ratios of the organ:

blood flow index [ml/100 g×$s_{-1}$]=maximum surge/surge time with surge time [s]=$t_{(y\,\%\,of\,the\,signal\,rise)} - t_{(x\,\%\,of\,the\,signal\,rise)}$, where t is time [s] and x and y are variables that define the beginning and end of the temporal surge interval of the transcerebral transport function that is being measured.

Referring to FIG. 1A, the system according to the present invention consists of a multichannel device with two or more spectroscopes, each consisting of a one pulsed, monochromatic light source M100, M101 having a wavelength in the range of the maximum absorption of the tracer substance and another pulsed light source R100, R101 that emits monochromatic light at a wavelength that is absorbed as little as possible by the tracer substance. The scattered and reflected light from source M100, M101, R100, and R101 is sensed by one or more light sensors L110, L210 and L111 and transmitted by optical waveguides to photomultipliers P120, P220, and P121, where the optical measuring and reference signal is converted into an electrical signal. The coordination between the pulsed light sources and signal conditioning S130 is performed by sequencing control A130. The cerebral dye curves determined in S130 are then conveyed to evaluator A140, e.g., digitally by an RS232 interface. Available to the evaluator A140 is also the data of the dye curve measured non-invasively by pulse densitometry in the arteries. An embodiment of the system for pulse densitometry, which can be assumed as known, is shown in the lower part of FIG. 1A.

Figure 1B:
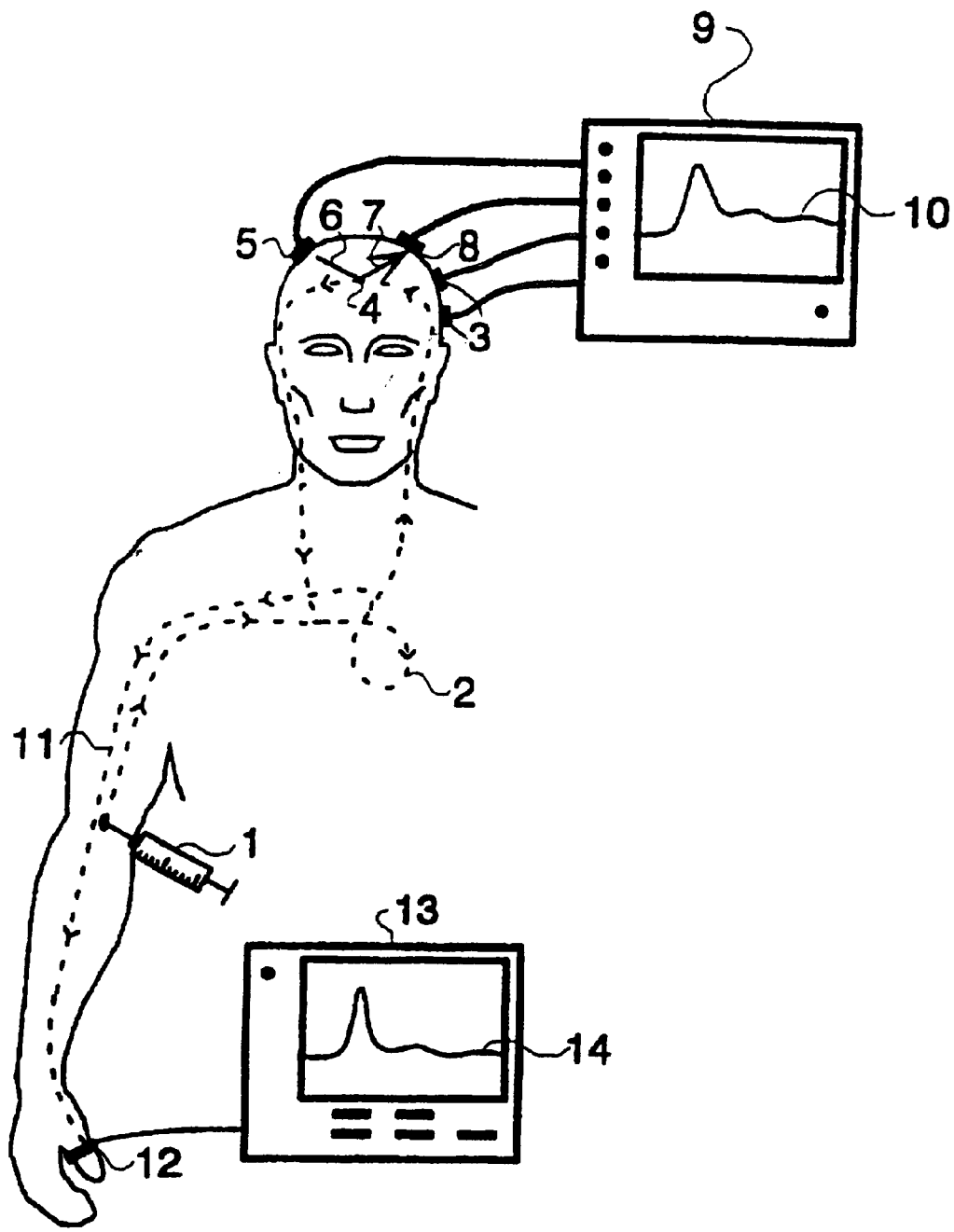
FIG. 1B illustrates an embodiment of the system according to the present invention for the noninvasive measurement of cerebral blood circulation in both hemispheres of the brain by near-infrared spectroscopy, pulse densitometry and intravenous administration of a tracer dye.

According to FIG. 1B, a bolus of tracer dye 1, having absorption properties in the near-infrared spectrum (e.g., indocyanine green) is intravenously injected. As shown by dashed line, the tracer dye reaches, by the venous vascular system, the right side of the heart and the pulmonary circulation to the left side of the heart, which discharges it into the arterial blood stream. A part of the dye bolus thus reaches the brain via the carotid arteries 2, and passes through its vascular system.

Two monochromatic light sources 3 placed on the surface of the scalp emit light through each hemisphere of the brain in the wavelength of the near-infrared spectrum. One of light sources, measuring wavelength, corresponds as near as possible to the absorption maximum of the tracer substance used. The other light source, reference wavelength, has a wavelength at which the tracer substance used has as few absorption properties as possible. Near-infrared light shown by reference numeral 4 penetrates the brain tissue beneath it non-invasively. In the tissue, the emitted near-infrared light of both the measuring and reference wavelengths is partially absorbed by endogenous chromophores (hemoglobin, cytochrome, etc.) and is partially reflected as scattered light. The latter is detected and quantified on each hemisphere by at least one light sensor 5 placed on the surface of the scalp homolaterally and coupled by fiber optic cable to a photomultiplier.

The passage of the intravenously administered tracer substance through the cerebral vascular system changes the optical density of the tissue by an amount within the absorption range of the dye., i.e., in the measurement range of the measuring wavelength, but not of the reference wavelength. From the ratio of the measuring and reference wavelength signals at the photomultipliers cerebral dye curve c(t)(6, 7) can be determined over time for each hemisphere of the brain.

Simultaneously, part of the dye bolus discharged from the left side of the heart reaches peripheral arterial vascular system 8, where the arterial dye curve 10 is determined by measurement through noninvasive pulse densitometry 9.

Figure 2:
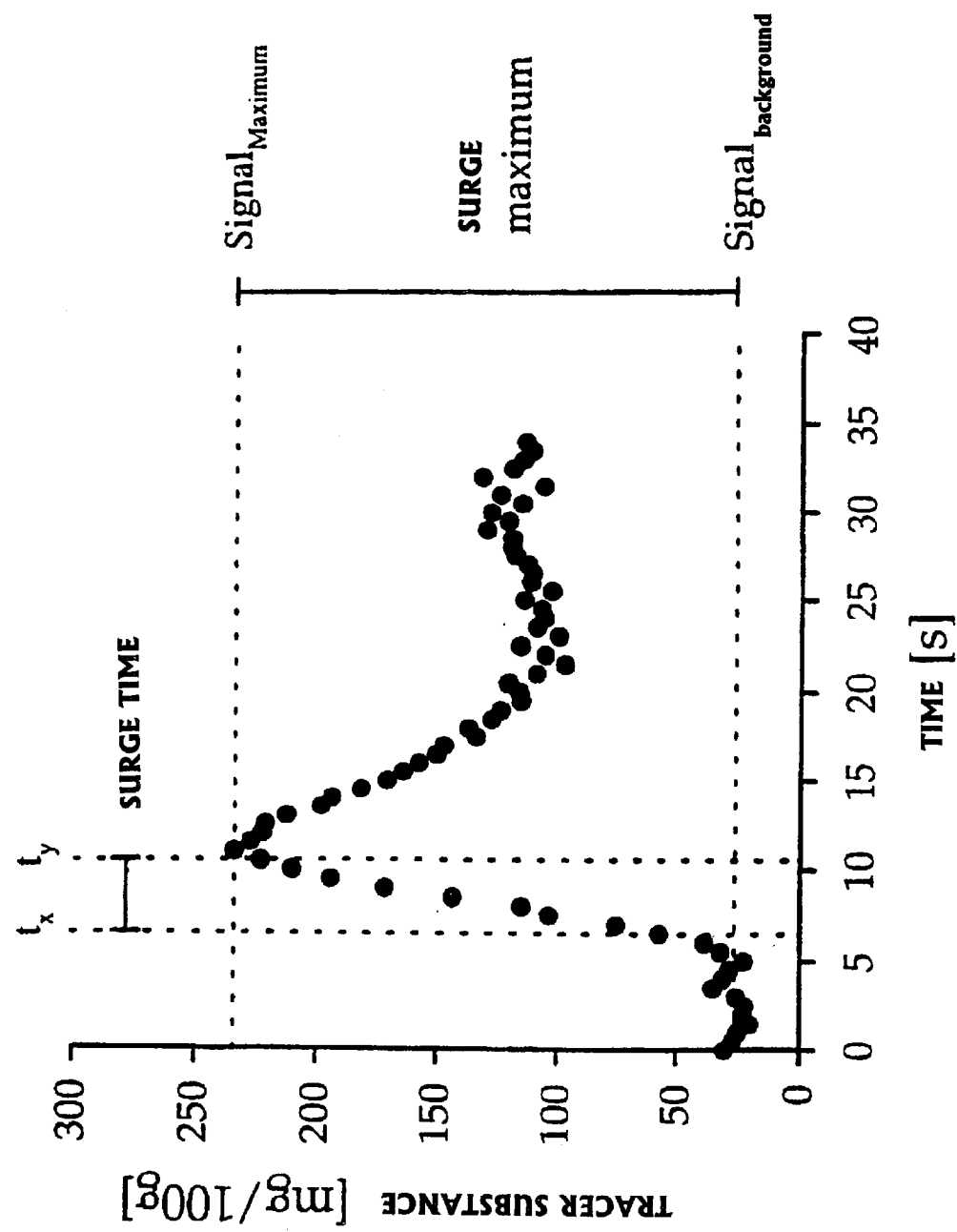
FIG. 2 is a graphical representation of arterial dye curves measured by pulse densitometry and cerebral dye curves measured by near-infrared spectroscopy.

After venous bolus injection of a sufficient amount of indicator, the dye curves shown as examples in FIG. 2 are recorded in the computer as an analog signal. As described herein, the arterial surge of the dye is determined non-invasively by measurement using pulse densitometry. The cerebral dye curves are detected separately for the right and left hemispheres of the brain. In doing so, the indicator dilution curves shown in FIG. 2 typically result. Also, shown in FIG. 2 is the arterial dye curve and the cerebral dye curves for the right and left hemispheres of the brain.

After correction for background signal, the arterial dye curve is adjusted with both cerebral dye curves so that the start of the surge for each curve overlaps. The respective transcerebral transport function for each hemisphere of the brain can be determined by the development of each cerebral dye curve with the corresponding arterial signal.

Figure 3:
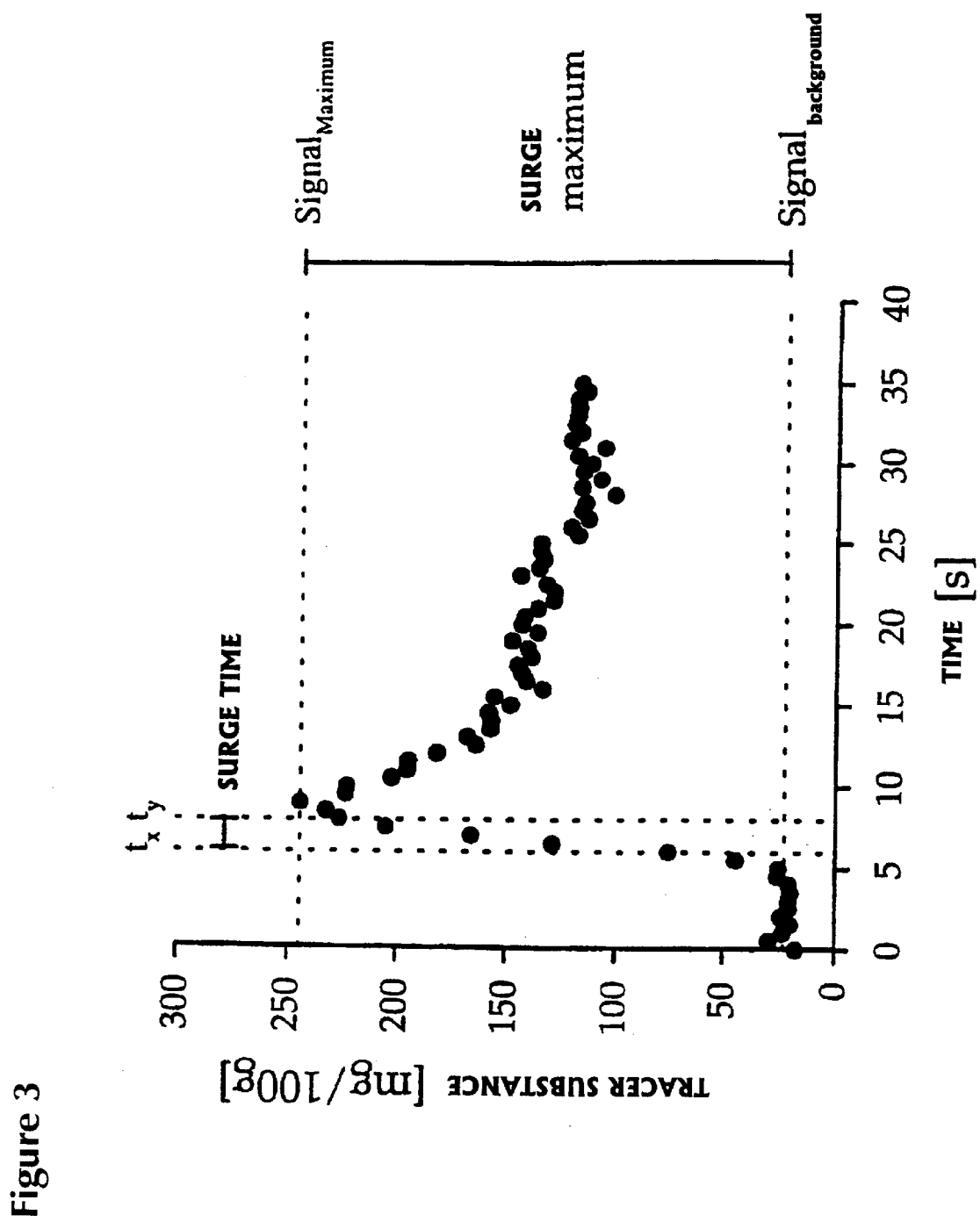
FIG. 3 is a graphical representation of a transcerebral transport function determined by the development of the arterial and cerebral dye curves.

FIG. 3 shows by way of example a transcerebral transport function g(t) that reflects the characteristic transmission properties of the cerebral vascular system.

In the transcerebral transport function, the intravascular surge of the dye leads to a rapid rise of the measuring signal, which reaches its maximum, surge maximum within a few seconds (in FIG. 3, 92.28 ml/100 g).

The surge time corresponds to time interval $t_2$, in which values z coincide with:

x % of the signal rise <z<y % of the signal rise.

In the measurement examples according to FIGS. 2 and 3, x and y are defined as:

x=10% of the signal rise=9.23 ml/100 g and
y=90% of the signal rise=83.05 ml/100 g.
The same applies for the example according to FIG. 3
$t_x$=2.40 s and $t_y$=5.58 s.
Thus the surge time is
$t_z$=$t_y$−$t_x$=3.18 s.
In this embodiment, a blood flow index of:
blood flow index [ml/100 g×s$^{-1}$]=surge maximum/($t_y$−$t_x$)= 92.28 ml/100 g/3.18 s=29.02 ml/100 g×s$^{-1}$
thus results.

The present invention allows for a process and a device that makes it possible to conduct user-friendly, noninvasive, rapid and repeated measurements of cerebral blood flow in a sickbed patient for the immediate (online) and easily understandable assessment and interpretation of the measured results. The system according to the present invention is distinguished especially by low equipment costs, high mobility and correspondingly quick availability.

In contrast to methods of determining the overall blood circulation in the brain, the process and system described in the present invention detect the blood circulation separately for the right and left hemisphere of the brain, i.e., the invention makes a regional breakdown that allows the quantitative determination of the relative blood circulation of the individual hemispheres of the brain. In this way the process of the present invention, in contrast to various conventional measuring techniques, offers the possibility of detecting regional distributions or distribution disruptions of the blood circulation in the brain between the right and left hemisphere.

Using the process according to the present invention, the passage of various tracer substances with absorption properties in the near-infrared spectrum can be detected using near-infrared spectroscopy. Accordingly, the passage of a tracer with absorption properties in the near-infrared spectrum can be detected at various wavelengths in the near-infrared range. Consequently the passage of a tracer with absorption properties in the near-infrared spectrum can be detected by NIRS using varying amounts and concentrations of tracer substance.

Several light sensors arranged spatially, allow for a regional or depth breakdown of the blood flow measurement.

The determination of the organ blood circulation by the process according to the present invention is not limited in principal to the determination of cerebral blood flow. Rather, with the aid of the process according to the invention, the passage of an intravascular tracer substance with absorption properties in the near-infrared spectrum can be detected in various organs for noninvasive determination of blood circulation.

To supplement the algorithm used in this invention and incorporating the arterial and cerebral dye curves measured non-invasively by the process/device illustrated, other circulatory parameters can also be quantified, i.e., cardiac output according to the Stewart-Hamilton method, intrathoracic blood volume as a product of average transit time (mtt) and cardiac output and—also with regional breakdown— relative cerebral blood volume as a product of average transit time (mtt) of transport function g(t) and of the relative blood flow index of the corresponding region.

Although the present invention has been described in relation to particular embodiments thereof, many other variations, modifications, and other uses will become apparent to those skilled in the art. It is preferred, therefore, that the present invention be limited not by the specific disclosure herein, but only by the appended claims.

What is claimed is:

1. A process for the noninvasive determination of blood flow, comprising the steps of:

intravenously administrating a predetermined amount of a tracer substance simultaneously into different regions of a patient, the tracer substance having absorption properties in the near-infrared spectrum;

determining a first dye curve by near-infrared spectroscopy; and determining a second dye curve by pulse densitometry, wherein the first and second dye curves are determined simultaneously.

2. The process according to claim 1, wherein the process detects cerebral blood flow and the step of administering the tracer substance comprises injecting the tracer substance into both cerebral hemispheres of a patient.

3. The process according to claim 2, wherein the first dye curve is a cerebral dye curve and the second dye curve is an arterial dye curve, the cerebral and arterial dye curves being determined simultaneously.

4. The process according to claim 3, wherein the tracer substance comprises an indicator dye, the indicator dye being used in varying amounts and concentrations such that the near-infrared spectroscopy can be performed at various wavelengths.

5. The process according to claim 4, further comprising the step of determining an intravascular transport function g(t) of the dye from the arterial and cerebral dye curves, wherein the correlation between transport function g(t), arterial dye curve a(t) and cerebral dye curve c(t) is determined by the following formula:

$$c(t) = {}_0\!\int^\infty g(t-u)a(u)du$$

wherein u is an auxiliary variable of the integration.

6. The process according to claim 5, wherein the step of determining the transport function g(t) further comprises varying parameters of the transport function by an interative, nonlinear matching process according to the principle of smallest squares, wherein the squares of differences between the measured cerebral dye curve c(t) and a convolution result of arterial dye curve a(t) are minimized according to the following formula:

$$[c(t) - {}_0\!\int^\infty g(t-u)a(u)du]^2.$$

7. The process according to claim 6, further comprising the step of describing the transport function g(t) by a logarithmic normal distribution according to the following formula:

$$g(t)=g_{lognor}(t,mtt,\sigma)=(1/\sqrt{2\pi}\sigma t)e^{-(ln t/mtt+\sigma^2/2)^2/2\sigma^2}$$

where mtt is the average transit time of the dye and $\sigma$ is the relative dispersion of the dye.

8. The process according to claim 7, wherein the transport function g(t) for a plurality of intra vascular compartments N having blood circulating there through at varying rates can be represented by the sum of two logarithmic normal distributions according to the formula:

$$g(t)=\Sigma\alpha_i g_{log\ nori}(t,\ mtt_i,\ \sigma_i).$$

wherein $\alpha_i>0$ and secondary condition $\Sigma\alpha_1=1$.

9. The process according to claim 8, further comprising the step of determining a blood flow index using the transcerebral dye transport function g(t) according to the formula:

blood flow index=surge maximum/surge time, wherein surge time $[s]=t_{(y\ \%\ of\ signal\ rise)}-t_{(x\ \%\ of\ signal\ rise)}$
and t is time [s] and x and y are variables that define the beginning and end of a temporal surge interval of the transcerebral transport function being measured.

10. The process according to claim 5, further comprising the step of quantifying by regional breakdown a relative cerebral blood volume as a product of average transit time (mtt) of transport function g(t) and of the relative blood flow index of the corresponding region.

11. The process according to claim 3, further comprising the step of performing a regional breakdown of blood circulation measurement by measuring, with near-infrared spectroscopy, the passage of the indicator dye using a plurality of light sensors arranged spatially on the patient.

12. The process according to claim 2, wherein the cerebral blood flow is detected regionally in different hemispheres of the brain simultaneously by simultaneous measurement using several monochromatic light sources, each light source having one or more subordinate light sensors.

13. The process according to claim 1, further comprising the step of quantifying cardiac output according to the Stewart-Hamilton equation.

14. The process according to claim 1, further comprising the step of quantifying intra thoracic blood volume as a product of average transit time (mtt) and cardiac output.

15. A system for noninvasive determination of cerebral blood flow comprising:

means for intravenously administrating a predetermined amount of a tracer substance, the tracer substance having absorption properties in the near-infrared spectrum;

a noninvasive pulse densitometry measuring device which measures an arterial dye curve;

a plurality of near-infrared spectroscopes, each said spectroscope having at least two pulsed monochromatic light sources in the wavelength range of the near-infrared spectrum for measuring a cerebral dye curve in each cerebral hemisphere, one light source produces a measuring wavelength at which the tracer substance has a maximum absorption rate, and the other light source produces a reference wavelength at which the tracer substance used has a minimum absorption rate; and a plurality of light sensors communicating with the light sources, the light sensors being connected to a photomultiplier for separate measurement of a cerebral dye curve for each cerebral hemisphere.

16. The system according to claim 15, further comprising an evaluation unit which detects a transport function from the measured arterial and cerebral dye curves.

17. The system according to claim 15, wherein the plurality of near-infrared spectroscopes are connected to the evaluation unit for detecting cerebral dye curves simultaneously over different brain areas for regional measurement of the cerebral blood flow.

* * * * *